(12) United States Patent
Strittmatter

(10) Patent No.: US 7,893,032 B2
(45) Date of Patent: Feb. 22, 2011

(54) NGR VARIANTS AND COMPOSITIONS THEREOF FOR SUPPRESSING AXONAL GROWTH INHIBITION

(75) Inventor: Stephen M. Strittmatter, Guilford, CT (US)

(73) Assignee: Yale University, New Haven, CT (US)

( * ) Notice: Subject to any disclaimer, the term of this patent is extended or adjusted under 35 U.S.C. 154(b) by 426 days.

(21) Appl. No.: 11/994,978

(22) PCT Filed: Jul. 7, 2006

(86) PCT No.: PCT/US2006/026634
§ 371 (c)(1),
(2), (4) Date: Jul. 14, 2008

(87) PCT Pub. No.: WO2007/008732
PCT Pub. Date: Jan. 18, 2007

(65) Prior Publication Data
US 2009/0054325 A1    Feb. 26, 2009

Related U.S. Application Data

(60) Provisional application No. 60/696,791, filed on Jul. 7, 2005.

(51) Int. Cl.
| A61K 38/08 | (2006.01) |
| A61K 38/10 | (2006.01) |
| A61K 38/16 | (2006.01) |
| C12N 1/21  | (2006.01) |
| C12N 15/00 | (2006.01) |
| C12N 5/00  | (2006.01) |
| C07H 21/00 | (2006.01) |

(52) U.S. Cl. ............ 514/21.6; 435/252.33; 435/252.35; 435/320.1; 435/325; 435/375; 530/324; 530/326; 530/327; 530/328; 530/350; 536/23.1

(58) Field of Classification Search .................. None
See application file for complete search history.

(56) References Cited

U.S. PATENT DOCUMENTS

| 5,250,414 | A  | 10/1993 | Schwab et al. |
| 5,684,133 | A  | 11/1997 | Schwab et al. |
| 5,858,708 | A  | 1/1999  | Bandman et al. |
| 6,025,333 | A  | 2/2000  | Schwab et al. |
| 6,475,753 | B1 | 11/2002 | Ruben et al. |
| 6,627,741 | B2 | 9/2003  | Ruben et al. |
| 6,774,216 | B2 | 8/2004  | Ruben et al. |
| 7,119,165 | B2 | 10/2006 | Strittmatter |
| 7,173,118 | B2 | 2/2007  | Strittmatter et al. |
| 2002/0012965 | A1 | 1/2002 | Strittmatter |
| 2002/0055139 | A1 | 5/2002 | Holtzman et al. |
| 2002/0072493 | A1 | 6/2002 | Eisenbach-Schwartz et al. |
| 2003/0113325 | A1 | 6/2003 | He et al. |
| 2003/0113326 | A1 | 6/2003 | He et al. |
| 2003/0124704 | A1 | 7/2003 | Strittmatter et al. |
| 2004/0029169 | A1 | 2/2004 | He et al. |
| 2005/0048520 | A1 | 3/2005 | Strittmatter et al. |
| 2005/0221420 | A1 | 10/2005 | Barske et al. |
| 2005/0271655 | A1 | 12/2005 | Lee et al. |
| 2007/0104713 | A1 | 5/2007 | Strittmatter et al. |
| 2008/0219984 | A1* | 9/2008 | Strittmatter ............... 424/139.1 |
| 2008/0274112 | A1* | 11/2008 | Lee et al. .................. 424/139.1 |

FOREIGN PATENT DOCUMENTS

| WO | WO 98/06841  | A3 | 2/1998  |
| WO | WO 99/46281  | A2 | 9/1999  |
| WO | WO 99/66041  | A1 | 12/1999 |
| WO | WO 00/05364  | A1 | 2/2000  |
| WO | WO 00/31235  | A2 | 6/2000  |
| WO | WO 00/32221  | A2 | 6/2000  |
| WO | WO 00/37638  | A2 | 6/2000  |
| WO | WO 00/53756  | A2 | 9/2000  |
| WO | WO 00/53758  | A2 | 9/2000  |
| WO | WO 00/58473  | A2 | 10/2000 |
| WO | WO 00/70050  | A1 | 11/2000 |
| WO | WO 00/73452  | A2 | 12/2000 |
| WO | WO 01/09162  | A2 | 2/2001  |
| WO | WO 01/51520  | A2 | 7/2001  |
| WO | WO 02/29059  | A2 | 4/2002  |
| WO | WO 03/018631 |    | 3/2003  |
| WO | WO 03/031462 | A2 | 4/2003  |
| WO | WO 03/035687 |    | 5/2003  |
| WO | WO 03/089470 | A1 | 10/2003 |
| WO | WO 2004/013157 | A2 | 2/2004 |
| WO | WO 2004/014311 | A2 | 2/2004 |
| WO | WO 2005/016955 | A2 | 2/2005 |

OTHER PUBLICATIONS

Budel, S. et al., "Genetic Variants of Nogo-66 Receptor with Possible Association to Schizophrenia Block Myelin Inhibition of Axon Growth," *J. Neurosci.* 28(49):13161-13172, Society of Neuroscience (Dec. 3, 2008).

Supplementary European Search Report for EP Application No. 06 78 6699, Munich, Germany, search completed on Nov. 10, 2009, 6 pgs.

Bandtlow, C.E., et al., "NI-35/250/Nogo-A: A Neurite Growth Inhibitor Restricting Structural Plasticity and Regeneration of Nerve Fibers in the Adult Vertebrate CNS," *Glia* 29:175-181, Wiley-Liss (2000).

Brittis, P.A., and Flanagan, J.G., "Nogo domains and a Nogo receptor: implications for axon regeneration," *Neuron* 30:11-14, Cell Press (2001).

(Continued)

*Primary Examiner*—Daniel E Kolker
*Assistant Examiner*—Gregory S Emch
(74) *Attorney, Agent, or Firm*—Sterne, Kessler, Goldstein & Fox P.L.L.C.

(57) ABSTRACT

The invention provides compositions and methods for interfering with Nogo-receptor mediated signaling and mediating axonal growth. The invention also provides methods for treating central nervous system diseases, disorders or injuries.

21 Claims, 3 Drawing Sheets

OTHER PUBLICATIONS

Chen, M.S., et al., Nogo-A is a Myelin-Associated Neurite Outgrowth Inhibitor and an Antigen for Monoclonal Antibody IN-1, *Nature* 403:434-439, Nature Publishing Group (2000).

Domeniconi, M., et al., "Myelin-Associated Glycoprotein Interacts with the Nogo66 Receptor to Inhibit Neurite Outgrowth," *Neuron* 35:283-290, Cell Press (2002).

Fournier, A.E., et al., "Identification of a Receptor Mediating Nogo-66 Inhibition of Axonal Regeneration," *Nature* 409: 341-346, Nature Publishing Group (2001).

Fournier, A.E., et al., "Characterization of the neuronal receptor mediating Nogo-66 inhibition of axonal regeneration," *J. Neurochem.* 78:105, Blackwell Publishing, Abstract No. S08-01 (2001).

Fournier, A.E., et al., "Nogo Receptor Domain Analysis," *Society for Neuroscience Abstracts* 27:670, Society for Neuroscience, Abstract No. 258.3, presented at the *Society for Neuroscience's 31st Annual Meeting*, San Diego, CA (2001).

GrandPre, T.J., et al., "Identification of the Nogo Inhibitor of Axon Regeneration as a Reticulon Protein," *Nature* 403:439-444, Nature Publishing Group (2000).

GrandPre, T.J., et al., "Functional Analysis of Nogo-66 and Nogo Receptor Domains," *Society for Neuroscience Abstracts* 27:670, Society for Neuroscience, Abstract No. 258.4, presented at the *Society for Neuroscience's 31st Annual Meeting*, San Diego, CA (2001).

Grandpré, T.J., and Strittmatter, S.M., "Nogo: A Molecular Determinant of Axonal Growth and Regeneration," *The Neuroscientist* 7:377-386, Sage Publications (2001).

GrandPré, T.J., et al., "Nogo-66 Receptor Antagonist Peptide Promotes Axonal Regeneration," *Nature* 417:547-551, Nature Publishing Group (2002).

Grimpe, B., et al., "The Critical Role of Basement Membrane-Independent Laminin Gamma 1 Chain During Axon Regeneration in the CNS," *J. Neurosci.* 22:3144-3160, Society for Neuroscience (2002).

Huber, A.B., et al., "Nogo-A, a Potent Inhibitor of Neurite Outgrowth and Regeneration," *Biol. Chem.* 381:407-419, Walter De Gruyter (2000).

Jones, L.L., et al., "NG2 is a major chondroitin sulfate proteoglycan produced after spinal cord injury and is expressed by macrophages and oligodendrocyte progenitors," *J. Neurosci.* 22:2792-2803, Society for Neuroscience (2002).

Lee, D.H., et al., "Targeting the Nogo receptor to treat central nervous system injuries," *Nat. Rev. Drug Discov.* 2:872-878, Nature Publishing Group (2003).

Li, M., et al., "Effect of soluble Nogo receptor treatment on functional and histological outcome after spinal cord injury in the rat," Biosis Database, Accession No. PREV200400194121, Abstract No. 80.22, *Presented at the 33rd Annual Meeting of the Society of Neuroscience*, New Orleans, LA (2003).

Li, W., et al., "Neutralization of NGR1 May Be Sufficient to Promote Rat DRG Neurite Outgrowth in the Presence of CNS Myelin," SFN 2003 Abstract Viewer & Itinerary Planner, Program No. 678.3, *Presented at the 33rd Annual Meeting of the Society of Neuroscience*, New Orleans, LA (2003).

Li, W., et al., "A Neutralizing Anti-Nogo66 Receptor Monoclonal Antibody Reverses Inhibition of Neurite Outgrowth by Central Nervous System Myelin," *J. Biol. Chem.* 42:43780-43788, The American Society for Biochemistry and Molecular Biology, Inc. (Oct. 2004).

Liu, B.P., et al., "Myelin-associated glycoprotein as a functional ligand for the Nogo-66 receptor," *Science* 297:1190-1193, American Association for the Advancement of Science (2002).

McKerracher, L., et al., "Identification of myelin-associated glycoprotein as a major myelin-derived inhibitor of neurite growth," *Neuron* 13:805-811, Cell Press (1994).

Merkler, D., et al., "Locomotor Recovery in Spinal Cord-Injured Rats Treated with an Antibody Neutralizing the Myelin-Associated Neurite Growth Inhibitor Nogo-A," *J. Neurosci.* 21:3665-3673, Society for Neuroscience (2001).

Mikol, D.D., and Stefansson, K., "A phosphatidylinositol-linked peanut agglutinin-binding glycoprotein in central nervous system myelin and on oligodendrocytes," *J. Cell Biol.* 106:1273-1279, Rockefeller University Press (1988).

Mukhopadhyay, G., et al., "A novel role for myelin-associated glycoprotein as an inhibitor of axonal regeneration," *Neuron* 13:757-767, Cell Press (1994).

Oertle, T., et al., "Nogo-A Inhibits Neurite Outgrowth and Cell Spreading with Three Discrete Regions," *J. Neurosci.* 23:5393-5406, Society for Neuroscience (2003).

Oudega, M., et al., "Neutralizing Antibodies Against Neurite Growth Inhibitor NI-35/250 Do Not Promote Regeneration of Sensory Axons in the Adult Rat Spinal Cord," *Neuroscience* 100:873-883, Elsevier Science Ltd. (2000).

Prinjha, R., et al., "Neurobiology: Inhibitor of Neurite Outgrowth in Humans," *Nature* 403:383-384, Nature Publishing Group (2000).

Raineteau, O., et al., "Sprouting and Regeneration After Pyramidotomy and Blockade of the Myelin-Associated Neurite Growth Inhibitors N1 35/250 in Adult Rats," *Eur. J. Neurosci.* 11:1486-1490, Blackwell Science (1999).

Raineteau, O., et al., "Functional Switch Between Motor Tracts in the Presence of the mAb IN-1 in the Adult Rat," *Proc. Natl. Acad. Sci. U.S.A.* 98:6929-6934, National Academy of Sciences (2001).

Spillmann, A.A., et al., "Identification and Characterization of a Bovine Neurite Growth Inhibitor (bNI-220)," *J. Bio. Chem.* 273:19283-19293, American Society for Biochemistry and Molecular Biology (1998).

Tatagiba, M., et al., "Regeneration of Injured Axons in the Adult Mammalian Central Nervous System," *Neurosurgery* 40:541-547, Lippincott Williams & Wilkins (1997).

Thallmair, M., et al., "Neurite Growth Inhibitors Restrict Plasticity and Functional Recovery Following Corticospinal Tract Lesions," *Nat. Neurosci.* 1:124-131, Nature Publishing Group (1998).

Wang, K.C., et al., "Oligodendrocyte-myelin glycoprotein is a Nogo receptor ligand that inhibits neurite outgrowth," *Nature* 417:941-944, Nature Publishing Group (2002).

Z'Graggen, W.J., et al., "Functional Recovery and Enhanced Corticofugal Plasticity After Unilateral Pyramidal Tract Lesion and Blockade of Myelin-Associated Neurite Growth Inhibitors in Adult Rats," *J. Neurosci.* 18:4744-4757, Society for Neuroscience (1998).

EMBL Database, Accession No. AC006549, Hu, P. et al., (Feb. 1999).

Zheng, B., "Genetic Deletion of the Nogo Receptor Does Not Reduce Neurite Inhibition in Vitro or Promote Corticospinal Tract Regeneration in Vivo," *Proc. Natl. Acad. Sci. USA.* 102: 1205-1210, National Academy of Sciences (2005).

* cited by examiner

SEQUENCE LISTING

<160> NUMBER OF SEQ ID NOS: 55

<210> SEQ ID NO 1
<211> LENGTH: 30
<212> TYPE: PRT
<213> ORGANISM: Artificial Sequence
<220> FEATURE:
<223> OTHER INFORMATION: Human mutant Nogo receptor polypeptide

<400> SEQUENCE: 1

```
Val Pro Pro Gly Asp Ser Pro Pro Gly Asn Gly Ser Gly Pro Gln His
  1               5                  10                  15

Ile Asn Asp Ser Pro Phe Gly Thr Leu Pro Gly Ser Ala Glu
             20                  25                  30
```

<210> SEQ ID NO 2
<211> LENGTH: 30
<212> TYPE: PRT
<213> ORGANISM: Artificial Sequence
<220> FEATURE:
<223> OTHER INFORMATION: Human mutant Nogo receptor polypeptide

<400> SEQUENCE: 2

```
Arg Val Pro Pro Gly Asp Ser Pro Pro Gly Asn Gly Ser Gly Pro Gln
  1               5                  10                  15

His Ile Asn Asp Ser Pro Phe Gly Thr Leu Pro Gly Ser Ala
             20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: Human mutant Nogo receptor polypeptide

<400> SEQUENCE: 3

```
Val Pro Pro Gly Asp Ser Pro Pro Gly Asn Gly Ser Gly Pro Trp His
  1               5                  10                  15

Ile Asn Asp Ser Pro Phe Gly Thr Leu Pro Gly Ser Ala Glu
             20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Human mutant Nogo receptor polypeptide

<400> SEQUENCE: 4

```
Arg Val Pro Pro Gly Asp Ser Pro Pro Gly Asn Gly Ser Gly Pro Trp
  1               5                  10                  15

His Ile Asn Asp Ser Pro Phe Gly Thr Leu Pro Gly Ser Ala
             20                  25                  30
```

<210> SEQ ID NO 5
<211> LENGTH: 30
<212> TYPE: PRT
<213> ORGANISM: Homo sapiens

<400> SEQUENCE: 5

```
Val Pro Pro Gly Asp Ser Pro Pro Gly Asn Gly Ser Gly Pro Arg His
  1               5                  10                  15
```

```
Ile Asn Asp Ser Pro Phe Gly Thr Leu Pro Gly Ser Ala Glu
         20                  25                  30

<210> SEQ ID NO 6
<211> LENGTH: 473
<212> TYPE: PRT
<213> ORGANISM: Homo sapiens

<400> SEQUENCE: 6

Met Lys Arg Ala Ser Ala Gly Gly Ser Arg Leu Leu Ala Trp Val Leu
 1               5                  10                  15

Trp Leu Gln Ala Trp Gln Val Ala Ala Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365
```

```
Pro Pro Gly Asn Gly Ser Gly Pro Arg His Ile Asn Asp Ser Pro Phe
        370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
            435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 7
<211> LENGTH: 473
<212> TYPE: PRT
<213> ORGANISM: Artificial Sequence
<220> FEATURE:
<223> OTHER INFORMATION: Human NgR R377Q mutant

<400> SEQUENCE: 7

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255
```

```
Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Gln His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 8
<211> LENGTH: 473
<212> TYPE: PRT
<213> ORGANISM: Artificial Sequence
<220> FEATURE:
<223> OTHER INFORMATION: Human NgR R377W mutant

<400> SEQUENCE: 8

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140
```

```
Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Trp His Ile Asn Asp Ser Pro Phe
370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
450                 455                 460

Val Leu Trp Thr Val Leu Gly Pro Cys
465                 470

<210> SEQ ID NO 9
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 9

Ala Leu Lys Gly Arg Val Pro Pro Gly Asp Ser Pro Gly Asn Gly
1               5                   10                  15

Ser Gly Pro Gln
            20
```

<210> SEQ ID NO 10
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 10

```
Leu Lys Gly Arg Val Pro Pro Gly Asp Ser Pro Pro Gly Asn Gly Ser
1               5                   10                  15

Gly Pro Gln His
            20
```

<210> SEQ ID NO 11
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 11

```
Lys Gly Arg Val Pro Pro Gly Asp Ser Pro Pro Gly Asn Gly Ser Gly
1               5                   10                  15

Pro Gln His Ile
            20
```

<210> SEQ ID NO 12
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 12

```
Gly Arg Val Pro Pro Gly Asp Ser Pro Pro Gly Asn Gly Ser Gly Pro
1               5                   10                  15

Gln His Ile Asn
            20
```

<210> SEQ ID NO 13
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 13

```
Arg Val Pro Pro Gly Asp Ser Pro Pro Gly Asn Gly Ser Gly Pro Gln
1               5                   10                  15

His Ile Asn Asp
            20
```

<210> SEQ ID NO 14
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 14

```
Val Pro Pro Gly Asp Ser Pro Pro Gly Asn Gly Ser Gly Pro Gln His
1               5                   10                  15

Ile Asn Asp Ser
```

-continued

```
<210> SEQ ID NO 15
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 15

Pro Pro Gly Asp Ser Pro Pro Gly Asn Gly Ser Gly Pro Gln His Ile
 1               5                  10                  15

Asn Asp Ser Pro
            20

<210> SEQ ID NO 16
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 16

Pro Gly Asp Ser Pro Pro Gly Asn Gly Ser Gly Pro Gln His Ile Asn
 1               5                  10                  15

Asp Ser Pro Phe
            20

<210> SEQ ID NO 17
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 17

Gly Asp Ser Pro Pro Gly Asn Gly Ser Gly Pro Gln His Ile Asn Asp
 1               5                  10                  15

Ser Pro Phe Gly
            20

<210> SEQ ID NO 18
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 18

Asp Ser Pro Pro Gly Asn Gly Ser Gly Pro Gln His Ile Asn Asp Ser
 1               5                  10                  15

Pro Phe Gly Thr
            20

<210> SEQ ID NO 19
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 19

Ser Pro Pro Gly Asn Gly Ser Gly Pro Gln His Ile Asn Asp Ser Pro
 1               5                  10                  15
```

```
Phe Gly Thr Leu
            20

<210> SEQ ID NO 20
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 20

Pro Pro Gly Asn Gly Ser Gly Pro Gln His Ile Asn Asp Ser Pro Phe
1               5                   10                  15

Gly Thr Leu Pro
            20

<210> SEQ ID NO 21
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 21

Pro Gly Asn Gly Ser Gly Pro Gln His Ile Asn Asp Ser Pro Phe Gly
1               5                   10                  15

Thr Leu Pro Gly
            20

<210> SEQ ID NO 22
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 22

Gly Asn Gly Ser Gly Pro Gln His Ile Asn Asp Ser Pro Phe Gly Thr
1               5                   10                  15

Leu Pro Gly Ser
            20

<210> SEQ ID NO 23
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 23

Asn Gly Ser Gly Pro Gln His Ile Asn Asp Ser Pro Phe Gly Thr Leu
1               5                   10                  15

Pro Gly Ser Ala
            20

<210> SEQ ID NO 24
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 24

Gly Ser Gly Pro Gln His Ile Asn Asp Ser Pro Phe Gly Thr Leu Pro
1               5                   10                  15
```

Gly Ser Ala Glu
            20

<210> SEQ ID NO 25
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 25

Ser Gly Pro Gln His Ile Asn Asp Ser Pro Phe Gly Thr Leu Pro Gly
1               5                   10                  15

Ser Ala Glu Pro
            20

<210> SEQ ID NO 26
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 26

Gly Pro Gln His Ile Asn Asp Ser Pro Phe Gly Thr Leu Pro Gly Ser
1               5                   10                  15

Ala Glu Pro Pro
            20

<210> SEQ ID NO 27
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 27

Pro Gln His Ile Asn Asp Ser Pro Phe Gly Thr Leu Pro Gly Ser Ala
1               5                   10                  15

Glu Pro Pro Leu
            20

<210> SEQ ID NO 28
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 28

Gln His Ile Asn Asp Ser Pro Phe Gly Thr Leu Pro Gly Ser Ala Glu
1               5                   10                  15

Pro Pro Leu Thr
            20

<210> SEQ ID NO 29
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 29

Ala Leu Lys Gly Arg Val Pro Pro Gly Asp Ser Pro Pro Gly Asn Gly

Ser Gly Pro Trp
         20

<210> SEQ ID NO 30
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 30

Leu Lys Gly Arg Val Pro Pro Gly Asp Ser Pro Pro Gly Asn Gly Ser
1               5                   10                  15

Gly Pro Trp His
         20

<210> SEQ ID NO 31
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 31

Lys Gly Arg Val Pro Pro Gly Asp Ser Pro Pro Gly Asn Gly Ser Gly
1               5                   10                  15

Pro Trp His Ile
         20

<210> SEQ ID NO 32
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 32

Gly Arg Val Pro Pro Gly Asp Ser Pro Pro Gly Asn Gly Ser Gly Pro
1               5                   10                  15

Trp His Ile Asn
         20

<210> SEQ ID NO 33
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 33

Arg Val Pro Pro Gly Asp Ser Pro Pro Gly Asn Gly Ser Gly Pro Trp
1               5                   10                  15

His Ile Asn Asp
         20

<210> SEQ ID NO 34
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 34

-continued

```
Val Pro Pro Gly Asp Ser Pro Gly Asn Gly Ser Gly Pro Trp His
1               5                   10                  15

Ile Asn Asp Ser
            20

<210> SEQ ID NO 35
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 35

Pro Pro Gly Asp Ser Pro Pro Gly Asn Gly Ser Gly Pro Trp His Ile
1               5                   10                  15

Asn Asp Ser Pro
            20

<210> SEQ ID NO 36
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 36

Pro Gly Asp Ser Pro Pro Gly Asn Gly Ser Gly Pro Trp His Ile Asn
1               5                   10                  15

Asp Ser Pro Phe
            20

<210> SEQ ID NO 37
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 37

Gly Asp Ser Pro Pro Gly Asn Gly Ser Gly Pro Trp His Ile Asn Asp
1               5                   10                  15

Ser Pro Phe Gly
            20

<210> SEQ ID NO 38
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 38

Asp Ser Pro Pro Gly Asn Gly Ser Gly Pro Trp His Ile Asn Asp Ser
1               5                   10                  15

Pro Phe Gly Thr
            20

<210> SEQ ID NO 39
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 39
```

```
Ser Pro Pro Gly Asn Gly Ser Gly Pro Trp His Ile Asn Asp Ser Pro
1               5                   10                  15

Phe Gly Thr Leu
            20

<210> SEQ ID NO 40
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 40

Pro Pro Gly Asn Gly Ser Gly Pro Trp His Ile Asn Asp Ser Pro Phe
1               5                   10                  15

Gly Thr Leu Pro
            20

<210> SEQ ID NO 41
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 41

Pro Gly Asn Gly Ser Gly Pro Trp His Ile Asn Asp Ser Pro Phe Gly
1               5                   10                  15

Thr Leu Pro Gly
            20

<210> SEQ ID NO 42
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 42

Gly Asn Gly Ser Gly Pro Trp His Ile Asn Asp Ser Pro Phe Gly Thr
1               5                   10                  15

Leu Pro Gly Ser
            20

<210> SEQ ID NO 43
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 43

Asn Gly Ser Gly Pro Trp His Ile Asn Asp Ser Pro Phe Gly Thr Leu
1               5                   10                  15

Pro Gly Ser Ala
            20

<210> SEQ ID NO 44
<211> LENGTH: 20
<212> TYPE: PRT
<213> ORGANISM: Artificial Sequence
<220> FEATURE:
<223> OTHER INFORMATION: Human mutant Nogo receptor polypeptide
```

-continued

```
<400> SEQUENCE: 44

Gly Ser Gly Pro Trp His Ile Asn Asp Ser Pro Phe Gly Thr Leu Pro
1               5                   10                  15

Gly Ser Ala Glu
            20

<210> SEQ ID NO 45
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 45

Ser Gly Pro Trp His Ile Asn Asp Ser Pro Phe Gly Thr Leu Pro Gly
1               5                   10                  15

Ser Ala Glu Pro
            20

<210> SEQ ID NO 46
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 46

Gly Pro Trp His Ile Asn Asp Ser Pro Phe Gly Thr Leu Pro Gly Ser
1               5                   10                  15

Ala Glu Pro Pro
            20

<210> SEQ ID NO 47
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 47

Pro Trp His Ile Asn Asp Ser Pro Phe Gly Thr Leu Pro Gly Ser Ala
1               5                   10                  15

Glu Pro Pro Leu
            20

<210> SEQ ID NO 48
<211> LENGTH: 20
<212> TYPE: PRT
<213> ORGANISM: Artificial Sequence
<220> FEATURE:
<223> OTHER INFORMATION: Human mutant Nogo receptor polypeptide

<400> SEQUENCE: 48

Trp His Ile Asn Asp Ser Pro Phe Gly Thr Leu Pro Gly Ser Ala Glu
1               5                   10                  15

Pro Pro Leu Thr
            20

<210> SEQ ID NO 49
<211> LENGTH: 8
<212> TYPE: PRT
<213> ORGANISM: Artificial Sequence
<220> FEATURE:
<223> OTHER INFORMATION: Synthetic FLAG polypeptide
```

```
<400> SEQUENCE: 49

Asp Tyr Lys Asp Asp Asp Asp Lys
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic FLAG polypeptide

<400> SEQUENCE: 50

Asp Tyr Lys Asp Glu Asp Asp Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Strep polypeptide tag

<400> SEQUENCE: 51

Ala Trp Arg His Pro Gln Phe Gly Gly
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic VSV-G polypeptide tag

<400> SEQUENCE: 52

Tyr Thr Asp Ile Glu Met Asn Arg Leu Gly Lys
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Synthetic poly-His tag

<400> SEQUENCE: 53

His His His His His His
1               5

<210> SEQ ID NO 54
<211> LENGTH: 13
<212> TYPE: PRT
<213> ORGANISM: Influenza virus

<400> SEQUENCE: 54

Tyr Pro Tyr Asp Val Pro Asp Tyr Ala Ile Glu Gly Arg
1               5                   10

<210> SEQ ID NO 55
<211> LENGTH: 11
<212> TYPE: PRT
<213> ORGANISM: Homo sapiens
```

-continued

```
<400> SEQUENCE: 55

Glu Gln Lys Leu Leu Ser Glu Glu Asp Leu Asn
1               5                   10
```

NGR VARIANTS AND COMPOSITIONS THEREOF FOR SUPPRESSING AXONAL GROWTH INHIBITION This application is the National Stage of International Application No. PCT/US2006/026634, filed Jul. 7, 2006, which published under PCT Article 21(2) in English, which claims the benefit of U.S. Provisional Application No. 60/696,791, filed Jul. 7, 2005; all of the above applications are incorporated herein by reference in their entireties.

FIELD OF THE INVENTION

This invention relates to neurobiology, neurology and pharmacology. More particularly, the invention relates to neurons and compositions and methods for mediating axonal growth.

BACKGROUND OF THE INVENTION

Axons and dendrites of neurons are long cellular extensions from neurons. The distal tip of an extending axon or neurite comprises a specialized region known as the growth cone, which senses the local environment and guides axonal growth toward the neuron's target cell. The guidance of growth at the cone involves various classes of adhesion molecules, intercellular signals, as well as factors that stimulate and inhibit growth cones.

Nerve cell function is greatly influenced by the contact between the neuron and other cells in its immediate environment. These cells include specialized glial cells, oligodendrocytes in the central nervous system (CNS), and Schwann cells in the peripheral nervous system (PNS), which ensheathe the neuronal axon with myelin (an insulating structure of multi-layered membranes). While CNS neurons have the capacity to regenerate after injury, they are inhibited from doing so because of the presence of inhibitory proteins present in myelin and possibly also by other types of molecules normally found in their local environment (Brittis and Flanagan, Neuron 2001, 30, pp. 11-14; Jones et al., J. Neurosci. 2002, 22, pp. 2792-2803; Grimpe et al., J. Neurosci. 2002, 22, pp. 3144-3160).

Several myelin inhibitory proteins that are found on oligodendrocytes have been characterized, e.g., NogoA (Chen et al., Nature, 2000, 403, 434-439; Grandpre et al., Nature 2000, 403, 439-444), myelin associated glycoprotein (MAG, McKerracher et al., Neuron 1994, 13, 805-811; Mukhopadhyay et al., Neuron 1994, 13, 757-767) and oligodendrocyte glycoprotein (OM-gp, Mikol and Stefansson, J. Cell. Biol. 1988, 106, 1273-1279). Each of these proteins has been separately shown to be a ligand for the neuronal Nogo receptor-1 ("NgR") (Wang et al., Nature 2002, 417, 941-944; Liu et al., Science, 2002, 297, 1190-93; Grandpre et al., Nature 2000, 403, 439-444; Chen et al., Nature, 2000, 403, 434-439; Domeniconi et al., Neuron, 2002, 35, 283-90). Nogo-66 is a 66 amino acid peptide from NogoA having the ability to inhibit neurite outgrowth and cause growth cone collapse. (Fournier et al., Nature 2001, 409, 341-346). Nogo receptor-1 is a GPI-anchored membrane protein that contains 8 leucine-rich repeats (Fournier et al., Nature 2001, 409, 341-346). Upon interaction with an inhibitory protein (e.g., NogoA, MAG and OM-gp), the Nogo receptor-1 complex transduces signals that lead to growth cone collapse and inhibition of neurite outgrowth.

Axonal damage is a key pathology in many injuries of the central nervous system (CNS), such as spinal cord injury, traumatic brain injury and stroke, as well as in multiple sclerosis (MS). A recently developed strategy for treating CNS injuries and CNS diseases is to interfere with the axonal growth inhibition that occurs through the interaction of myelin proteins with their axonal receptors, such as NgR. For example, the anti-NogoA antibody IN-1 was shown to improve functional recovery in rats that had undergone spinal cord transection. (Lee et al., Nature Reviews 2003, 2, 1-7.) In addition, a 40 residue peptide known as NEP1-40, an antagonist of NogoA, was shown to attenuate the effects of myelin or Nogo-66 on growth cone collapse and neurite outgrowth, and improved the outcome in vivo following spinal cord injury. (Lee et al., Nature Reviews 2003, 2, 1-7.) Although these reagents have shown great promise in treating injuries to the CNS, there remains a need in the art for additional compounds that inhibit NgR signaling and/or attenuate myelin-mediated growth cone collapse and/or inhibit neurite outgrowth inhibition.

SUMMARY OF THE INVENTION

The present invention is based on the discovery that certain mutant Nogo receptor polypeptides are useful for suppressing axonal growth inhibition in CNS neurons. Based on this and other discoveries, the invention features molecules and methods useful for suppressing axonal growth inhibition in CNS neurons.

In some embodiments, the invention provides an isolated polypeptide comprising an amino acid sequence selected from the group consisting of:

| | |
|---|---|
| VPPGDSPPGNGSGPQHINDSPFGTLPGSAE; | (SEQ ID NO: 1) |
| RVPPGDSPPGNGSGPQHINDSPFGTLPGSA; | (SEQ ID NO: 2) |
| VPPGDSPPGNGSGPWHINDSPFGTLPGSAE; | (SEQ ID NO: 3) |
| and | |
| RVPPGDSPPGNGSGPWHINDSPFGTLPGSA. | (SEQ ID NO: 4) |

In some embodiments, the invention provides an isolated nucleic acid molecule encoding a polypeptide of the invention. In some embodiments, the invention provides a vector comprising the isolated nucleic acid molecule. In some embodiments, the invention provides a host cell transformed to contain a nucleic acid molecule or vector of the invention.

In some embodiments, the invention provides a method for producing a polypeptide comprising the step of culturing a host cell of the invention under conditions in which the protein encoded by said nucleic acid molecule is expressed.

In some embodiments, the invention provides a chimeric polypeptide comprising a polypeptide of the invention. In some embodiments, the invention provides a pharmaceutical composition comprising a polypeptide of the invention.

In some embodiments, the invention provides an antibody that binds to a polypeptide comprising an amino acid sequence selected from the group consisting of:

| | |
|---|---|
| VPPGDSPPGNGSGPQHINDSPFGTLPGSAE; | (SEQ ID NO: 1) |
| RVPPGDSPPGNGSGPQHINDSPFGTLPGSA; | (SEQ ID NO: 2) |
| VPPGDSPPGNGSGPWHINDSPFGTLPGSAE; | (SEQ ID NO: 3) |
| and | |
| RVPPGDSPPGNGSGPWHINDSPFGTLPGSA. | (SEQ ID NO: 4) |

In some embodiments, the antibody is a monoclonal antibody. In some embodiments, the antibody is a polyclonal antibody.

In some embodiments, the invention provides a nonhuman transgenic animal which comprises a nucleic acid molecule of the invention.

In some embodiments, the invention provides a method of treating a central nervous system disease, disorder or injury in a mammal comprising administering an effective amount of a polypeptide of the invention or antibody of the invention. In some embodiments, the disease, disorder or injury is selected from the group consisting of: multiple sclerosis, ALS, Huntington's disease, Alzheimer's disease, Parkinson's disease, diabetic neuropathy, stroke, traumatic brain injuries, spinal cord injury, optic neuritis, and glaucoma.

In some embodiments, the invention provides a method of treating a central nervous system disease, disorder or injury in a mammal by in vivo gene therapy, comprising administering to a mammal, at or near the site of the disease, disorder or injury, a viral vector comprising the nucleotide sequence that encodes a polypeptide of the invention so that the polypeptide is expressed from the nucleotide sequence in the mammal in an amount sufficient to reduce inhibition of axonal extension by neurons at or near the site of the injury. In some embodiments, the viral vector is selected from the group consisting of an adenoviral vector, a lentiviral vector, a baculoviral vector, an Epstein Barr viral vector, a papovaviral vector, a vaccinia viral vector, and a herpes simplex viral vector. In some embodiments, the viral vector is administered by a route selected from the group consisting of topical administration, intraocular administration, parenteral administration, intrathecal administration, subdural administration and subcutaneous administration. In some embodiments, wherein the disease, disorder or injury is selected from the group consisting of: cerebral injury, spinal cord injury, stroke, demyelinating diseases, e.g., multiple sclerosis, monophasic demyelination, encephalomyelitis, multifocal leukoencephalopathy, panencephalitis, Marchiafava-Bignami disease, Spongy degeneration, Alexander's disease, Canavan's disease, metachromatic leukodystrophy and Krabbe's disease.

DETAILED DESCRIPTION OF THE INVENTION

Figure 1:
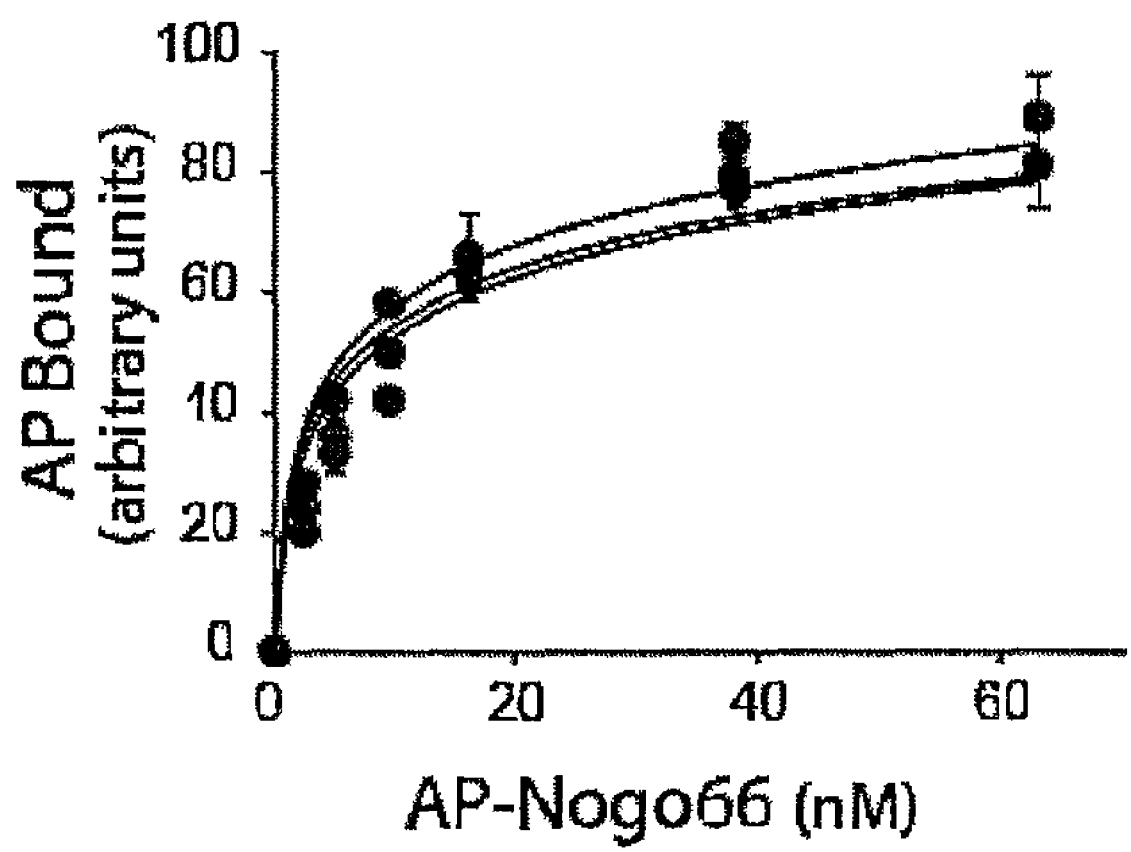
FIG. 1 shows the results of Nogo-66 binding assays conducted over a range of ligand concentrations.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

Throughout this specification and claims, the word "comprise," or variations such as "comprises" or "comprising," indicate the inclusion of any recited integer or group of integers but not the exclusion of any other integer or group of integers. In order to further define this invention, the following terms and definitions are provided.

As used herein, a "therapeutically effective amount" refers to an amount effective, at dosages and for periods of time necessary, to achieve the desired therapeutic result.

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "patient" means a mammal, e.g., a human.

As used herein, "fusion protein" means a protein comprising a first polypeptide fused to a second, heterologous, polypeptide.

The invention relates to the discovery that certain mutant Nogo receptor (NgR) polypeptides are useful for suppressing axonal growth inhibition in CNS neurons. Thus, the site of action of the NgR polypeptides of the invention in vivo is the nervous system.

The present invention includes NgR polypeptides that suppress myelin-mediated axonal growth inhibition. In other words, the NgR polypeptides of the invention stimulate axonal growth under conditions in which axonal growth is normally inhibited. Thus, the NgR polypeptides of the invention are useful in treating injuries and disease conditions that can be alleviated by the stimulation of axonal growth in the CNS.

Exemplary diseases, disorders and injuries that may be treated using molecules and methods of the invention include, but are not limited to, cerebral injury, spinal cord injury, stroke, demyelinating diseases, e.g., multiple sclerosis, monophasic demyelination, encephalomyelitis, multifocal leukoencephalopathy, panencephalitis, Marchiafava-Bignami disease, Spongy degeneration, Alexander's disease, Canavan's disease, metachromatic leukodystrophy and Krabbe's disease. (See U.S. Patent Appl. No. 2005/0048520, and the references cited therein.)

As used herein, the expression "NgR polypeptide" means a polypeptide comprising at least 10 consecutive amino acids of a polypeptide selected from the group consisting of: (a) the wild-type NgR protein (SEQ ID NO:6); (b) the R377Q mutant NgR protein (SEQ ID NO:7); or (c) the R377W mutant NgR protein (SEQ ID NO:8); wherein the NgR polypeptide includes the amino acid at position 377 of the respective polypeptide.

The aforementioned amino acid sequences are as follows

```
Wild-Type Full-Length Human NgR (SEQ ID NO: 6):
MKRASAGGSRLLAWVLWLQAWQVAAPCPGACVCYNEPKVTTSCPQQGLQA

VPVGIPAASQRIFLHGNRISHVPAASFRACRNLTILWLHSNVLARIDAAA
```

-continued

```
FTGLALLEQLDLSDNAQLRSVDPATFHGLGRLHTLHLDRCGLQELGPGLF
RGLAALQYLYLQDNALQALPDDTFRDLGNLTHLFLHGNRISSVPERAFRG
LHSLDRLLLHQNRVAHVHPHAFRDLGRLMTLYLFANNLSALPTEALAPLR
ALQYLRLNDNPWVCDCRARPLWAWLQKFRGSSSEVPCSLPQRLAGRDLKR
LAANDLQGCAVATGPYHPIWTGRATDEEPLGLPKCCQPDAADKASVLEPG
RPASAGNALKGRVPPGDSPPGNGSGP☐HINDSPFGTLPGSAEPPLTAVRP
EGSEPPGFPTSGPRRRPGCSRKNRTRSHCRLGQAGSGGGGTGDSEGSGAL
PSLTCSLTPLGLALVLWTVLGPC.

Full length human NgR R377Q mutant (SEQ ID NO: 7):
MKRASAGGSRLLAWVLWLQAWQVAAPCPGACVCYNEPKVTTSCPQQGLQA
VPVGIPAASQRIFLHGNRISHVPAASFRACRNLTILWLHSNVLARIDAAA
FTGLALLEQLDLSDNAQLRSVDPATFHGLGRLHTLHLDRCGLQELGPGLF
RGLAALQYLYLQDNALQALPDDTFRDLGNLTHLFLHGNRISSVPERAFRG
LHSLDRLLLHQNRVAHVHPHAFRDLGRLMTLYLFANNLSALPTEALAPLR
ALQYLRLNDNPWVCDCRARPLWAWLQKFRGSSSEVPCSLPQRLAGRDLKR
LAANDLQGCAVATGPYHPIWTGRATDEEPLGLPKCCQPDAADKASVLEPG
RPASAGNALKGRVPPGDSPPGNGSGP☐HINDSPFGTLPGSAEPPLTAVRP
EGSEPPGFPTSGPRRRPGCSRKNRTRSHCRLGQAGSGGGGTGDSEGSGAL
PSLTCSLTPLGLALVLWTVLGPC.

Full length human NgR R377W mutant (SEQ ID NO: 8):
MKRASAGGSRLLAWVLWLQAWQVAAPCPGACVCYNEPKVTTSCPQQGLQA
VPVGIPAASQRIFLHGNRISHVPAASFRACRNLTILWLHSNVLARIDAAA
FTGLALLEQLDLSDNAQLRSVDPATFHGLGRLHTLHLDRCGLQELGPGLF
RGLAALQYLYLQDNALQALPDDTFRDLGNLTHLFLHGNRISSVPERAFRG
LHSLDRLLLHQNRVAHVHPHAFRDLGRLMTLYLFANNLSALPTEALAPLR
ALQYLRLNDNPWVCDCRARPLWAWLQKFRGSSSEVPCSLPQRLAGRDLKR
LAANDLQGCAVATGPYHPIWTGRATDEEPLGLPKCCQPDAADKASVLEPG
RPASAGNALKGRVPPGDSPPGNGSGP☐HINDSPFGTLPGSAEPPLTAVRP
EGSEPPGFPTSGPRRRPGCSRKNRTRSHCRLGQAGSGGGGTGDSEGSGAL
PSLTCSLTPLGLALVLWTVLGPC.
**The boxed amino acid in the above-listed se-
quences is amino acid number 377.
```

Exemplary NgR polypeptides of the invention are listed below:

```
VPPGDSPPGNGSGP☐HINDSPFGTLPGSAE;        (SEQ ID NO: 1)
RVPPGDSPPGNGSGP☐HINDSPFGTLPGSA;        (SEQ ID NO: 2)
VPPGDSPPGNGSGP☐HINDSPFGTLPGSAE;        (SEQ ID NO: 3)
and
RVPPGDSPPGNGSGP☐HINDSPFGTLPGSA.        (SEQ ID NO: 4)
```

Additional exemplary NgR polypeptides of the invention are set forth in Table I.

TABLE I

| SEQ ID NO: | sequence |
|---|---|
| 9 | ALKGRVPPGDSPPGNGSGP☐ |
| 10 | LKGRVPPGDSPPGNGSGP☐H |
| 11 | KGRVPPGDSPPGNGSGP☐HI |
| 12 | GRVPPGDSPPGNGSGP☐HIN |
| 13 | RVPPGDSPPGNGSGP☐HIND |
| 14 | VPPGDSPPGNGSGP☐HINDS |
| 15 | PPGDSPPGNGSGP☐HINDSP |
| 16 | PGDSPPGNGSGP☐HINDSPF |
| 17 | GDSPPGNGSGP☐HINDSPFG |
| 18 | DSPPGNGSGP☐HINDSPFGT |
| 19 | SPPGNGSGP☐HINDSPFGTL |
| 20 | PPGNGSGP☐HINDSPFGTLP |
| 21 | PGNGSGP☐HINDSPFGTLPG |
| 22 | GNGSGP☐HINDSPFGTLPGS |
| 23 | NGSGP☐HINDSPFGTLPGSA |
| 24 | GSGP☐HINDSPFGTLPGSAE |
| 25 | SGP☐HINDSPFGTLPGSAEP |
| 26 | GP☐HINDSPFGTLPGSAEPP |
| 27 | P☐HINDSPFGTLPGSAEPPL |
| 28 | ☐HINDSPFGTLPGSAEPPLT |
| 29 | ALKGRVPPGDSPPGNGSGP☐ |
| 30 | LKGRVPPGDSPPGNGSGP☐H |
| 31 | KGRVPPGDSPPGNGSGP☐HI |
| 32 | GRVPPGDSPPGNGSGP☐HIN |
| 33 | RVPPGDSPPGNGSGP☐HIND |
| 34 | VPPGDSPPGNGSGP☐HINDS |
| 35 | PPGDSPPGNGSGP☐HINDSP |
| 36 | PGDSPPGNGSGP☐HINDSPF |
| 37 | GDSPPGNGSGP☐HINDSPFG |
| 38 | DSPPGNGSGP☐HINDSPFGT |
| 39 | SPPGNGSGP☐HINDSPFGTL |
| 40 | PPGNGSGP☐HINDSPFGTLP |
| 41 | PGNGSGP☐HINDSPFGTLPG |
| 42 | GNGSGP☐HINDSPFGTLPGS |
| 43 | NGSGP☐HINDSPFGTLPGSA |
| 44 | GSGP☐HINDSPFGTLPGSAE |
| 45 | SGP☐HINDSPFGTLPGSAEP |

TABLE I-continued

| SEQ ID NO: | sequence |
|---|---|
| 46 | GP⊡HINDSPFGTLPGSAEPP |
| 47 | P⊡HINDSPFGTLPGSAEPPL |
| 48 | ⊡HINDSPFGTLPGSAEPPLT |

**The boxed amino acid in the above-listed sequences is amino acid number 377.

NgR polypeptides of the invention may comprise any of the aforementioned amino acid sequences along with additional (e.g., 1, 2, 4, 6, 8, 10, 20, 30, 40, 50, 100, 200, or more) amino acids covalently attached to the N- and/or C-terminal amino acids of the sequences shown above.

The NgR polypeptides of the invention, in certain embodiments, include polypeptides comprising one or more of the aforementioned amino acid sequences (e.g., SEQ ID NOs: 1-4 and 9-48). The invention also includes NgR polypeptides comprising amino acid sequences that are homologous to any one of SEQ ID NOs: 1-4 and 9-48. For example, NgR polypeptides of the invention may comprise amino acids sequences that are at least 50%, 55%, 60%, 65%, 70%, 75%, 80%, 85%, 90%, 91%, 92%, 93%, 94%, 95%, 96%, 97%, 98% or 99% homologous to any one of SEQ ID NOs: 1-4 and 9-48, as long as the amino acid corresponding to amino acid number 377 of wild-type full-length human NgR (SEQ ID NO:6) is a Q or a W.

An amino acid sequence that is homologous to a reference amino acid sequence (e.g., an amino acid sequence that is at least 90% homologous to SEQ ID NO:1) is an amino acid sequence characterized by a homology at the amino acid level of at least a specified percentage. Homologous amino acid sequences include those amino acid sequences which contain conservative amino acid substitutions, wherein the NgR polypeptides comprising such homologous sequences are capable of suppressing Nogo-mediated axonal cell growth inhibition or growth cone collapse. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482-489, which is incorporated herein by reference in its entirety).

In methods of the present invention, an NgR polypeptide of the invention can be administered directly as a preformed polypeptide, or indirectly through a nucleic acid vector. In some embodiments of the invention, an NgR polypeptide of the invention is administered in a treatment method that includes: (1) transforming or transfecting an implantable host cell with a nucleic acid, e.g., a vector, that expresses an NgR polypeptide of the invention; and (2) implanting the transformed host cell into a mammal, at the site of a disease, disorder or injury. For example, the transformed host cell can be implanted at the site of a chronic lesion of MS. In some embodiments of the invention, the implantable host cell is removed from a mammal, temporarily cultured, transformed or transfected with an isolated nucleic acid encoding an NgR polypeptide of the invention, and implanted back into the same mammal from which it was removed. The cell can be, but is not required to be, removed from the same site at which it is implanted. Such embodiments, sometimes known as ex vivo gene therapy, can provide a continuous supply of the NgR polypeptide of the invention, localized at the site of action, for a limited period of time.

Additional exemplary NgR polypeptides of the invention and methods and materials for obtaining these molecules for practicing the present invention are described below.

Fusion Proteins and Conjugated Polypeptides

Some embodiments of the invention involve the use of an NgR polypeptide that is not the full-length NgR protein, e.g., polypeptide fragments of the NgR signaling domain, fused to a heterologous polypeptide moiety to form a fusion protein. Such fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the NgR polypeptide moiety of the invention or to be cleavable, in vitro or in vivo. Heterologous moieties to accomplish these other objectives are known in the art.

As an alternative to expression of a fusion protein, a chosen heterologous moiety can be preformed and chemically conjugated to the NgR polypeptide moiety of the invention. In most cases, a chosen heterologous moiety will function similarly, whether fused or conjugated to the NgR polypeptide moiety. Therefore, in the following discussion of heterologous amino acid sequences, unless otherwise noted, it is to be understood that the heterologous sequence can be joined to the NgR polypeptide moiety in the form of a fusion protein or as a chemical conjugate.

Pharmacologically active polypeptides such as NgR polypeptides may exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as polypeptide fragments of the NgR signaling domain can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known. Examples include serum albumins such as, e.g., bovine serum albumin (BSA) or human serum albumin (HSA).

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA,* 89:1904-08 (1992) and Syed et al., *Blood* 89:3243-52 (1997), HSA can be used to form a fusion protein or polypeptide conjugate that displays pharmacological activity by virtue of the NgR polypeptide moiety while displaying significantly increased in vivo stability, e.g., 10-fold to 100-fold higher. The C-terminus of the HSA can be fused to the N-terminus of the NgR polypeptide moiety. Since HSA is a naturally secreted protein, the HSA signal sequence can be exploited to obtain secretion of the fusion protein into the cell culture medium when the fusion protein is produced in a eukaryotic, e.g., mammalian, expression system.

Some embodiments of the invention employ an NgR polypeptide moiety fused to a hinge and Fc region, i.e., the C-terminal portion of an Ig heavy chain constant region. Potential advantages of an NgR-polypeptide-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is generally used, e.g., an IgG1 Fc region or IgG4 Fc region. Materials and methods for constructing and expressing DNA encoding Fc fusions are known in the art and can be applied to obtain fusions without undue experimentation. Some embodiments of the invention employ a fusion protein such as those described in Capon et al., U.S. Pat. Nos. 5,428,130 and 5,565,335.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.*, 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of a immunofusin protein containing the Fc region and the NgR polypeptide moiety.

In some embodiments, the DNA sequence may encode a proteolytic cleavage site between the secretion cassette and the NgR polypeptide moiety. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes an NgR polypeptide of the invention and used for the expression and secretion of the polypeptide. Host cells that are typically used include immortal hybridoma cells, myeloma cells, 293 cells, Chinese hamster ovary (CHO) cells, Hela cells, and COS cells.

Fully intact, wild-type Fc regions display effector functions that normally are unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the CH2 domain of the Fc region of IgE, such that this site does not interfere with the efficient secretion of the immunofusin. Transmembrane domain sequences, such as those present in IgM, also are generally deleted.

The IgG1 Fc region is most often used. Alternatively, the Fc region of the other subclasses of immunoglobulin gamma (gamma-2, gamma-3 and gamma-4) can be used in the secretion cassette. The IgG1 Fc region of immunoglobulin gamma-1 is generally used in the secretion cassette and includes at least part of the hinge region, the CH2 region, and the CH3 region. In some embodiments, the Fc region of immunoglobulin gamma-1 is a CH2-deleted-Fc, which includes part of the hinge region and the CH3 region, but not the CH2 region. A CH2-deleted-Fc has been described by Gillies et al., *Hum. Antibod. Hybridomas* 1:47 (1990). In some embodiments, the Fc region of one of IgA, IgD, IgE, or IgM, is used.

NgR-polypeptide-moiety-Fc fusion proteins can be constructed in several different configurations. In one configuration the C-terminus of the NgR polypeptide moiety is fused directly to the N-terminus of the Fc hinge moiety. In a slightly different configuration, a short polypeptide, e.g., 2-10 amino acids, is incorporated into the fusion between the N-terminus of the NgR polypeptide moiety and the C-terminus of the Fc moiety. Such a linker provides conformational flexibility, which may improve biological activity in some circumstances. If a sufficient portion of the hinge region is retained in the Fc moiety, the NgR-polypeptide-moiety-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link an NgR polypeptide of the invention to serum albumin. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, SIAB. Linkers that provide a protected or non-protected thiol for reaction with sulfhydryl groups to product a reducible linkage include SPDP, SMPT, SATA, and SATP. Such reagents are commercially available (e.g., Pierce Chemical Company, Rockford, Ill.).

Conjugation does not have to involve the N-terminus of an NgR polypeptide of the invention or the thiol moiety on serum albumin. For example, NgR-polypeptide-albumin fusions can be obtained using genetic engineering techniques, wherein the NgR polypeptide moiety is fused to the serum albumin gene at its N-terminus, C-terminus, or both.

NgR polypeptides of the invention can be fused to a polypeptide tag. The term "polypeptide tag," as used herein, is intended to mean any sequence of amino acids that can be attached to, connected to, or linked to an NgR polypeptide and that can be used to identify, purify, concentrate or isolate the NgR polypeptide. The attachment of the polypeptide tag to the NgR polypeptide may occur, e.g., by constructing a nucleic acid molecule that comprises: (a) a nucleic acid sequence that encodes the polypeptide tag, and (b) a nucleic acid sequence that encodes an NgR polypeptide. Exemplary polypeptide tags include, e.g., amino acid sequences that are capable of being post-translationally modified, e.g., amino acid sequences that are biotinylated. Other Exemplary polypeptide tags include, e.g., amino acid sequences that are capable of being recognized and/or bound by an antibody (or fragment thereof) or other specific binding reagent. Polypeptide tags that are capable of being recognized by an antibody (or fragment thereof) or other specific binding reagent include, e.g., those that are known in the art as "epitope tags." An epitope tag may be a natural or an artificial epitope tag. Natural and artificial epitope tags are known in the art, including, e.g., artificial epitopes such as FLAG, Strep, or polyhistidine peptides. FLAG peptides include the sequence Asp-Tyr-Lys-Asp-Asp-Asp-Asp-Lys (SEQ ID NO:49) or Asp-Tyr-Lys-Asp-Glu-Asp-Asp-Lys (SEQ ID NO:50)) (Einhauer, A. and Jungbauer, A., *J. Biochem. Biophys. Methods* 49:1-3: 455-465 (2001)). The Strep epitope has the sequence Ala-Trp-Arg-His-Pro-Gln-Phe-Gly-Gly (SEQ ID NO:51). The VSV-G epitope can also be used and has the sequence Tyr-Thr-Asp-Ile-Glu-Met-Asn-Arg-Leu-Gly-Lys (SEQ ID NO:52). Another artificial epitope is a poly-His sequence having six histidine residues (His-His-His-His-His-His (SEQ ID NO:53). Naturally-occurring epitopes include the influenza virus hemagglutinin (HA) sequence Tyr-Pro-Tyr-Asp-Val-Pro-Asp-Tyr-Ala-Ile-Glu-Gly-Arg (SEQ ID NO:54) recognized by the monoclonal antibody 12CA5 (Murray et al., *Anal. Biochem.* 229:170-179 (1995)) and the eleven amino acid sequence from human c-myc (Myc) recognized by the monoclonal antibody 9E10 (Glu-Gln-Lys-Leu-Leu-Ser-Glu-Glu-Asp-Leu-Asn (SEQ ID NO:55) (Manstein et al., *Gene* 162:129-134 (1995)). Another useful epitope is the tripeptide Glu-Glu-Phe which is recognized by the monoclonal antibody YL ½. (Stammers et al. *FEBS Lett.* 283:298-302 (1991)).

In certain embodiments, the NgR polypeptide and the polypeptide tag may be connected via a linking amino acid sequence. As used herein, a "linking amino acid sequence" may be an amino acid sequence that is capable of being recognized and/or cleaved by one or more proteases. Amino acid sequences that can be recognized and/or cleaved by one or more proteases are known in the art. Exemplary amino acid sequences are those that are recognized by the following proteases: factor VIIa, factor Ixa, factor Xa, APC, t-PA, u-PA, trypsin, chymotrypsin, enterokinase, pepsin, cathepsin B, H, L, S, D, cathepsin G, renin, angiotensin converting enzyme, matrix metalloproteases (collagenases, stromelysins, gelatinases), macrophage elastase, Cir, and Cis. The amino acid sequences that are recognized by the aforementioned proteases are known in the art. Exemplary sequences recognized by certain proteases can be found, e.g., in U.S. Pat. No. 5,811,252.

Polypeptide tags can facilitate purification using commercially available chromatography media.

In some embodiments of the invention, an NgR polypeptide fusion construct is used to enhance the production of an NgR polypeptide moiety in bacteria. In such constructs a bacterial protein normally expressed and/or secreted at a high level is employed as the N-terminal fusion partner of an NgR polypeptide of the invention. See, e.g., Smith et al., *Gene* 67:31 (1988); Hopp et al., *Biotechnology* 6:1204 (1988); La Vallie et al., *Biotechnology* 11:187 (1993).

By fusing an NgR polypeptide moiety at the amino and carboxy termini of a suitable fusion partner, bivalent or tetravalent forms of an NgR polypeptide of the invention can be obtained. For example, an NgR polypeptide moiety can be fused to the amino and carboxy termini of an Ig moiety to produce a bivalent monomeric polypeptide containing two NgR polypeptide moieties. Upon dimerization of two of these monomers, by virtue of the Ig moiety, a tetravalent form of an NgR polypeptide is obtained. Such multivalent forms can be used to achieve increased binding affinity for the target. Multivalent forms of an NgR polypeptide of the invention also can be obtained by placing NgR polypeptide moieties in tandem to form concatamers, which can be employed alone or fused to a fusion partner such as Ig or HSA.

Conjugated Polymers (Other than Polypeptides)

Some embodiments of the invention involve an NgR polypeptide of the invention wherein one or more polymers are conjugated (covalently linked) to the NgR polypeptide. Examples of polymers suitable for such conjugation include polypeptides (discussed above), sugar polymers and polyalkylene glycol chains. Typically, but not necessarily, a polymer is conjugated to the NgR polypeptide of the invention for the purpose of improving one or more of the following: solubility, stability, or bioavailability.

The class of polymer generally used for conjugation to an NgR polypeptide of the invention is a polyalkylene glycol. Polyethylene glycol (PEG) is most frequently used. PEG moieties, e.g., 1, 2, 3, 4 or 5 PEG polymers, can be conjugated to each NgR polypeptide to increase serum half life, as compared to the NgR polypeptide alone. PEG moieties are nonantigenic and essentially biologically inert. PEG moieties used in the practice of the invention may be branched or unbranched.

The number of PEG moieties attached to the NgR polypeptide and the molecular weight of the individual PEG chains can vary. In general, the higher the molecular weight of the polymer, the fewer polymer chains attached to the polypeptide. Usually, the total polymer mass attached to the Sp35 polypeptide is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the NgR polypeptide through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the NgR polypeptide. Free carboxylic groups, suitably activated carbonyl groups, hydroxyl, guanidyl, imidazole, oxidized carbohydrate moieties and mercapto groups of the NgR polypeptide (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the NgR polypeptide moiety. Preferably, at least 50% of the biological activity (as demonstrated, e.g., in any of the assays described herein or known in the art) of the NgR polypeptide is retained, and most preferably nearly 100% is retained.

The polymer can be conjugated to the NgR polypeptide using conventional chemistry. For example, a polyalkylene glycol moiety can be coupled to a lysine epsilon amino group of the NgR polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors*, 3: 4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation"

includes without limitation the following types of linkages between the therapeutic protein and a water-soluble polymer such as PEG: amide, carbamate, urethane, and the like. See, e.g., *Bioconjugate Chem.* 5: 133-140, 1994. Reaction parameters are generally selected to avoid temperature, solvent, and pH conditions that would damage or inactivate the NgR polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with an NgR polypeptide of the invention in the presence of a reducing agent. In addition, one can manipulate the reaction conditions to favor PEGylation substantially only at the N-terminal amino group of the NgR polypeptide, i.e. a mono-PEGylated protein. In either case of mono-PEGylation or poly-PEGylation, the PEG groups are typically attached to the protein via a —$CH_2$—NH— group. With particular reference to the —$CH_2$— group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono $C_1$-$C_{10}$ alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated NgR polypeptides of the invention generally includes the steps of (a) reacting an NgR polypeptide of the invention with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/NgR polypeptide generally includes the steps of: (a) reacting an NgR polypeptide of the invention with a reactive PEG molecule under reductive alkylation conditions, at a pH suitable to pen-nit selective modification of the N-terminal amino group of NgR; and (b) obtaining the reaction product(s).

For a substantially homogeneous population of mono-polymer/NgR polypeptide, the reductive alkylation reaction conditions are those that permit the selective attachment of the water-soluble polymer moiety to the N-terminus of an NgR polypeptide of the invention. Such reaction conditions generally provide for pKa differences between the lysine side chain amino groups and the N-terminal amino group. For purposes of the present invention, the pH is generally in the range of 3-9, typically 3-6.

NgR polypeptides of the invention can include a tag, e.g., a moiety that can be subsequently released by proteolysis. Thus, the lysine moiety can be selectively modified by first reacting a His-tag modified with a low-molecular-weight linker such as Traut's reagent (Pierce Chemical Company, Rockford, Ill.) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce Chemical Company, Rockford, Ill.). Similarly one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the NgR polypeptide. Coupling can be effected using, e.g., a maleimide group, a vinylsulfone group, a haloacetate group, or a thiol group.

Optionally, the NgR polypeptide is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

The NgR polypeptides of the invention, in certain embodiments, are soluble polypeptides. Methods for making a polypeptide soluble or improving the solubility of a polypeptide are well known in the art.

Antibodies

The invention also includes antibodies that bind to an NgR polypeptide of the invention. For example, the invention includes antibodies that bind to an NgR polypeptide comprising one or more amino acid sequence selected from the group consisting of SEQ ID NOs: 1-4 and 9-48. Preferably, the antibodies of the invention are specific for NgR polypeptides having either a Q or a W at the amino acid position corresponding to amino acid number 377 of the wild-type full-length human NgR (SEQ ID NO:6). For instance, exemplary antibodies of the invention will bind to an NgR polypeptide having either a Q or a W at the amino acid position corresponding to amino acid number 377 of the wild-type full-length human NgR (SEQ ID NO:6) but will not bind (or will bind only weakly) to an NgR polypeptide having an R at the amino acid position corresponding to amino acid number 377 of the wild-type full-length human NgR (SEQ ID NO:6).

The term "antibody," as used herein, includes, e.g., native antibodies, intact monoclonal antibodies, polyclonal antibodies, multispecific antibodies (e.g., bispecific antibodies) formed from at least two intact antibodies, antibody fragments (e.g., antibody fragments that bind to and/or recognize one or more antigens), humanized antibodies, human antibodies (Jakobovits et al., *Proc. Natl. Acad. Sci. USA* 90:2551 (1993); Jakobovits et al., *Nature* 362:255-258 (1993); Bruggermann et al., *Year in Immunol.* 7:33 (1993); U.S. Pat. Nos. 5,591,669 and 5,545,807), antibodies and antibody fragments isolated from antibody phage libraries (McCafferty et al., *Nature* 348:552-554 (1990); Clackson et al., *Nature* 352:624-628 (1991); Marks et al., *J. Mol. Biol.* 222:581-597 (1991); Marks et al., *Bio/Technology* 10:779-783 (1992); Waterhouse et al., *Nucl. Acids Res.* 21:2265-2266 (1993)). Methods for making and using antibodies are well known in the art. (See, e.g., WO 00/67796 and references cited therein.)

Polynucleotides

The present invention also includes isolated polynucleotides comprising a nucleotide sequence that encodes an amino acid sequence selected from the group consisting of SEQ ID NOs:1-4 and 9-48. The invention also includes polynucleotides that hybridize under moderately stringent or high stringency conditions to the noncoding strand, or complement, of a polynucleotide that encodes any one of SEQ ID NOs:1-4 and 9-48. Stringent conditions are known to those skilled in the art and can be found in CURRENT PROTOCOLS 1N MOLECULAR BIOLOGY, John Wiley & Sons, N.Y. (1989), 6.3.1-6.3.6.

Vectors

Vectors comprising nucleic acids encoding NgR polypeptides of the invention may also be used to produce polypeptide for use in the methods of the invention. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad Laboratories, Hercules, Calif.), pPL and pKK223. Any suitable prokaryotic host can be used to express a recombinant DNA molecule encoding a protein used in the methods of the invention.

Eukaryotic cell expression vectors are known in the art and are commercially available. Typically, such vectors contain convenient restriction sites for insertion of the desired DNA segment. Exemplary vectors include pSVL and pKSV-10, pBPV-1, pm12d, pTDT1 (ATCC 31255), retroviral expression vector pMIG, adenovirus shuttle vector pDC315, and AAV vectors.

Eukaryotic cell expression vectors may include a selectable marker, e.g., a drug resistance gene. The neomycin phosphotransferase (neo) gene is an example of such a gene (Southern et al., *J. Mol. Anal. Genet.* 1:327-341 (1982)).

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (Adm1P)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr–host cells with methotrexate selection/amplification) and the neo gene (for G418 selection).

Nucleic acid molecules encoding NgR polypeptides of the invention, and vectors comprising these nucleic acid molecules, can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

Mammalian cell lines available as hosts for expression are known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Host Cells

Host cells for expression of an NgR polypeptide of the invention for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

Gene Therapy

An NgR polypeptide of the invention can be produced in vivo in a mammal, e.g., a human patient, using a gene-therapy approach to treatment of a nervous-system disease, disorder or injury in which antagonizing NgR-mediating signaling would be therapeutically beneficial. This involves administration of a suitable NgR polypeptide encoding nucleic acid operably linked to suitable expression control sequences. Generally, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno-associated virus (AAV) vectors. The viral vector can be a replication-defective viral vector. Adenoviral vectors that have a deletion in its E1 gene or E3 gene are typically used. When an adenoviral vector is used, the vector usually does not have a selectable marker gene.

Pharmaceutical Compositions

The NgR polypeptides, polynucleotides, vectors and host cells of the invention may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, NgR polypeptides of the invention act in the nervous system to inhibit NgR-mediated signaling. Accordingly, in the methods of the invention, the NgR polypeptides are administered in such a way that they cross the blood-brain barrier. This crossing can result from the physico-chemical properties inherent in the NgR polypeptide molecule itself, from other components in a pharmaceutical formulation, or from the use of a mechanical device such as a needle, cannula or surgical instruments to breach the blood-brain barrier. Where the NgR polypeptide is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the NgR polypeptide is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including, emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an NgR polypeptide of the invention that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of an NgR polypeptide. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular NgR polypeptide used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the NgR polypeptides are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the NgR polypeptide is administered. In some embodiments of the invention, the dosage is 0.01-1.0 mg/kg body weight per day. In some embodiments, the dosage is 0.001-0.5 mg/kg body weight per day.

Supplementary active compounds also can be incorporated into the compositions used in the methods of the invention. For example, a NgR polypeptide of the invention, or a fusion protein thereof, may be coformulated with and/or coadministered with one or more additional therapeutic agents.

The invention encompasses any suitable delivery method for a NgR polypeptide to a selected target tissue, including bolus injection of an aqueous solution or implantation of a controlled-release system. Use of a controlled-release implant reduces the need for repeat injections.

The NgR polypeptides used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-91 (1992); Gaspar et al., "Permanent $^{125}$I Implants for Recurrent Malignant Gliomas," *Int. J. Radiation Oncology Biol. Phys.* 43(5): 977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise an NgR polypeptide of the invention dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments, an NgR polypeptide of the invention is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer an NgR polypeptide according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

In Vitro Methods

The present invention also includes methods of suppressing neuronal cell growth inhibition in vitro. For example, the invention includes in vitro methods for stimulating neuronal cell growth in the presence of factors that, under normal circumstances, cause neuronal cell growth inhibition or growth cone collapse.

The methods, according to this aspect of the invention, comprise contacting a neuronal cell that expresses a Nogo receptor with an agent that causes NgR-mediated growth inhibition in the presence and absence of an isolated NgR polypeptide of the invention. As used herein, the expression "agent that causes NgR-mediated growth inhibition" means any compound that interacts with a component of the Nogo receptor signal transduction pathway (e.g., NgR or NgR interacting proteins), thereby stimulating the inhibition of neuronal cell growth or growth cone collapse. Exemplary agents that cause NgR-mediated growth inhibition include, e.g., Nogo (e.g., NogoA, Nogo-66), myelin-associated glycoprotein (MAG), oligodendrocyte glycoprotein (OMgp), and fragments and derivatives thereof that inhibit the growth of cells that express the Nogo receptor. Myelin itself is another exemplary agent that causes NgR-mediated growth inhibition.

The neuronal cell used in the practice of the in vitro methods of the invention may, in certain embodiments, express an endogenous Nogo receptor. In other embodiments, the neuronal cell expresses an exogenous Nogo receptor from a vector. The neuronal cell may express both an endogenous Nogo receptor and an exogenous Nogo receptor.

The methods according to this aspect of the invention may comprise monitoring the extent of neuronal growth inhibition or growth cone collapse in the presence and/or absence of an isolated NgR polypeptide of the invention. The in vitro methods of the invention can be used to characterize the extent to which candidate NgR polypeptides are able to suppress neuronal cell growth inhibition or growth cone collapse that normally occurs in the presence of an agent that causes NgR-mediated growth inhibition. Thus, the methods of the invention are useful for identifying and characterizing the full range of NgR polypeptides having the ability to suppress neuronal cell growth inhibition. The methods according to this aspect of the invention may be performed in high throughput formats.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Dominant-Negative Mutations in the Nogo Receptor Signaling Domain

Two mutations at amino acid R377 of the NgR polypeptide have been identified. These mutations are R377Q and R377W. The mutant NgR protein having the R377Q mutation is designated "NgR-R377Q" or "NgR$^Q$" (SEQ ID NO:7) and the mutant NgR protein having the R377W mutation is designated "NgR-R377W" or "NgR$^W$" (SEQ ID NO:8).

The ability of NgR-R377Q and NgR-R377W to bind Nogo-66, a protein known to bind wild-type NgR, was assessed. COS-7 cells were transfected with plasmids encoding either the full length wild-type human NgR protein ("NgR$^{WT}$"), the NgR-R377Q mutant protein ("NgRQ") or the NgR-R377W mutant protein ("NgR$^W$"). Comparable levels of expression of the different NgRs was confirmed by immunostaining and immunoblotting.

Thirty-six hours later, varying concentration of alkaline-phosphatase (AP)-Nogo-66 were allowed to bind for 16 hours at 4° C. Washed cells were fixed with 3.7% formaldehyde in PBS for 15 minutes. Endogenous AP activity was heat inactivated at 67° C. for 6-12 hours. Bound AP fusion protein was assessed in the presence of nitro blue tetrazolium and 5-bromo-4-chloro-3-indolyl phosphate and quantified using NIH image software. It was found that the mutant proteins exhibit no difference from wild-type in their ability to bind Nogo-66 (FIG. 1). In co-immunoprecipitation experiments, it was found that the mutant NgR proteins exhibited no difference from wild-type in their ability to bind p75NTR and Lingo-1, proteins that are also known to bind to wild-type NgR.

Figure 2A:
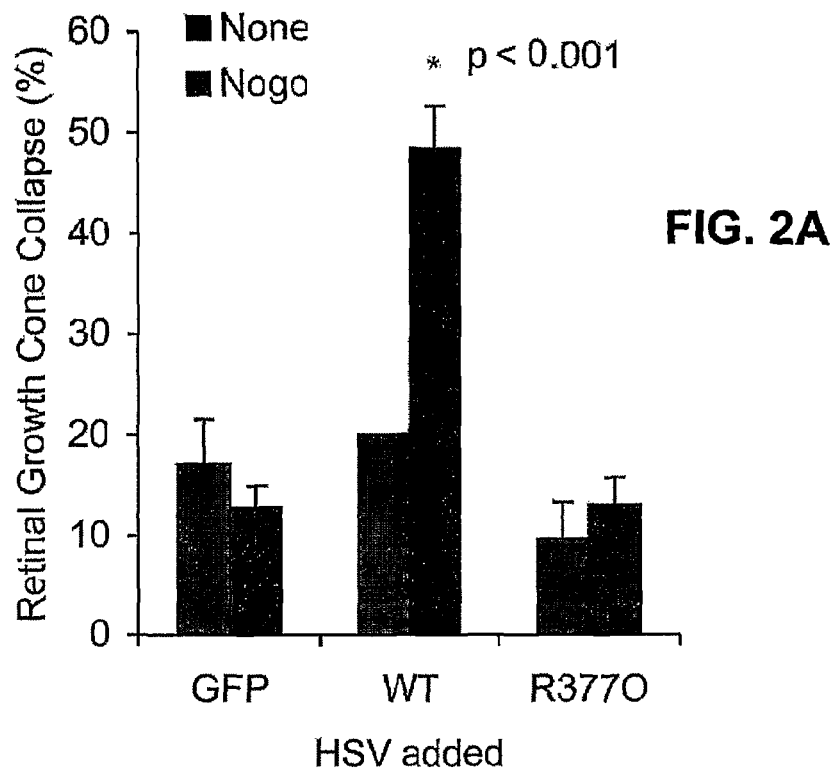
FIG. 2 quantifies collapsed E7 (A) or E13 (B) chick DRG growth cones expressing the indicated proteins and exposed (dark) or not exposed (light) to 100 µM Nogo-66.

The signaling ability of the NgR mutant proteins was directly assessed by expressing the proteins in chick DRG neurons and monitoring Nogo-induced growth cone collapse. In young E7 (embryonic day 7) DRG neurons, endogenous NgR is not present and the cells do not respond to Nogo inhibition. E7 cells that expressed wild-type NgR from a viral vector exhibited growth cone collapse in the presence of Nogo; E7 cells that expressed NgR-R377Q, however, did not. (FIG. 2A). Thus, NgR-R377Q is inactive in signal transduction.

Figure 2B:
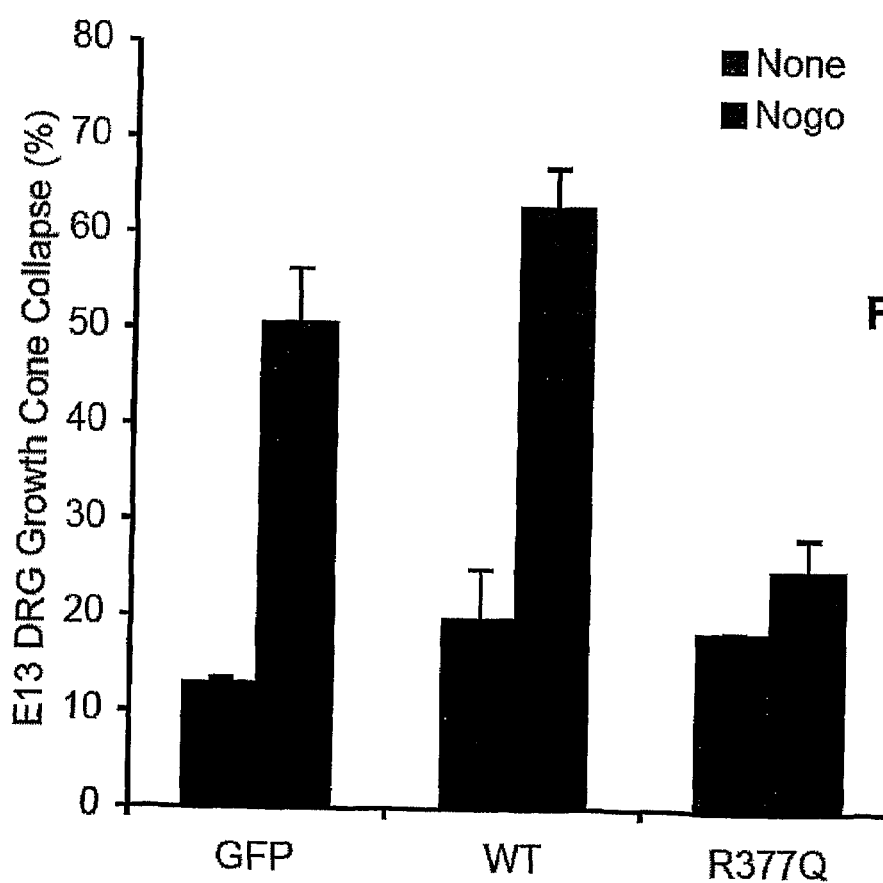

At E13, DRG neurons express NgR and respond to Nogo with growth cone collapse that is not altered by overexpression of wild-type NgR. (FIG. 2B). Overexpression of NgR-R377Q, on the other hand, significantly decreased the extent of Nogo-induced growth cone collapse in E13 DRG cells. (FIG. 2B). Thus, NgR-R377Q is a dominant negative protein.

Example 2

Dominant Negative Fragments of the R377Q and R377W Mutants

Synthetic peptides of 30 amino acids centered on residue 377 of either wild type NgR (REP$^{WT}$) (SEQ ID NO:5), NgR-R377Q (REP$^Q$) (SEQ ID NO:1), or NgR-R377W (REP$^W$) (SEQ ID NO:3) were synthesized and tested in growth cone collapse assays. The amino acid sequences of these peptides are as follows:

```
REP^WT:
VPPGDSPPGNGSGP R HINDSPFGTLPGSAE;    (SEQ ID NO: 5)

REP^Q:
VPPGDSPPGNGSGP Q HINDSPFGTLPGSAE;    (SEQ ID NO: 1)

and

REP^W:
vppgdsppgngsgp W hindspfgtlpgsae.    (SEQ ID NO: 3)
```

The boxed amino acid in the above-listed sequences is amino acid number 377 in the corresponding full-length protein.

Figure 3B:
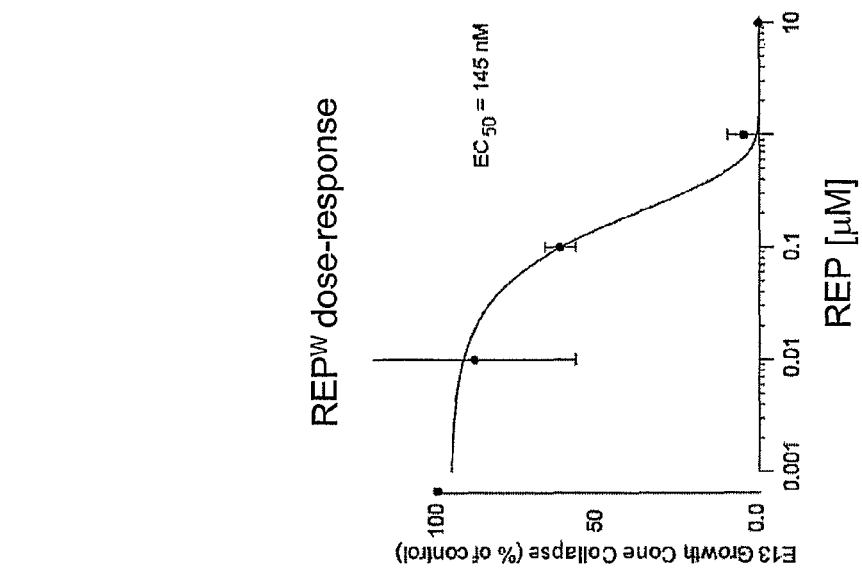
FIG. 3B shows the dose-response curve of REP$^W$ in an E13 growth cone collapse assay.
Figure 3A:
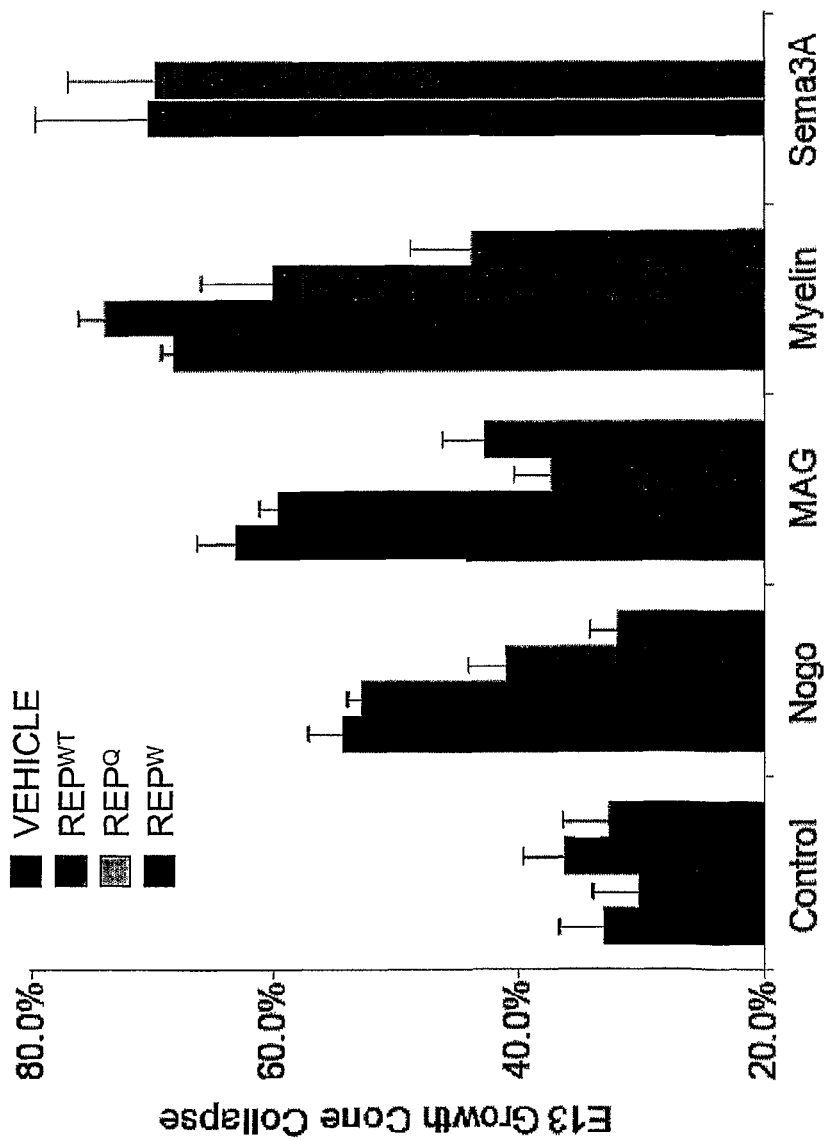
FIG. 3A shows growth cone collapse of E13 chick DRG growth cones in the presence of 100 nM Nogo-66, 100 nM MAG-Fc, 2 µg myelin protein/ml or 10 nM Sema3A. Collapse was assessed without peptide ("VEHICLE"); with 1 µM wild-type 30-amino-acid peptide ("REP$^{WT}$"; SEQ ID NO:5); with 1 µM R377Q peptide ("REP$^Q$"; SEQ ID NO:1); or 1 µM R377W peptide ("REP$^W$"; SEQ ID NO:3).

None of the peptides induced growth cone collapse by themselves when added to E13 DRG neurons. (FIG. 3A). However, REP$^Q$ and REP$^W$ were shown to significantly inhibit Nogo-induced growth cone collapse. (FIG. 3A). REP$^Q$ and REP$^W$ also significantly inhibited the growth cone collapse that is observed in the presence of MAG or myelin protein. (FIG. 3A). In these experiments, E13 DRG growth cone collapse was assessed in the presence of 100 nM Nogo-66, 100 nM MAG-Fc, 2 μg myelin protein/ml or 10 nM Sema3A. Collapse was assessed with vehicle only, 1 μM REP$^{WT}$, 1 μM REP$^Q$ or 1 μM REP$^W$.

The REP$^W$ polypeptide is a potent blocker of Nogo-induced collapse, with an EC50 of approximately 145 nM. (FIG. 3B).

This experiment indicates that NgR polypeptides, such as REP$^Q$ and REP$^W$, are useful in treating injuries characterized by axonal damage by virtue of their ability to suppress axonal growth inhibition in the presence of molecules such as MAG, OMgp, and NogoA which, under normal circumstances, cause Nogo receptor-mediated axonal growth inhibition.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated NgR polypeptide comprising:
   (a) at least 10 consecutive amino acids of the full length human NgR R377Q mutant (SEQ ID NO:7); or
   (b) at least 10 consecutive amino acids of the full length human NgR R377W mutant (SEQ ID NO:8);
   wherein said at least 10 consecutive amino acids includes the amino acid at position 377 of said full length human NgR R377Q or R377W mutant.

2. The isolated NgR polypeptide of claim 1, wherein said polypeptide comprises at least 10 consecutive amino acids of the full length human NgR R377Q mutant (SEQ ID NO:7).

3. The isolated NgR polypeptide of claim 1, wherein said polypeptide comprises at least 10 consecutive amino acids of the full length human NgR R377W mutant (SEQ ID NO:8).

4. The isolated NgR polypeptide of claim 1, wherein said polypeptide comprises at least 12 consecutive amino acids of said full length human NgR R377Q or R377W mutant.

5. The isolated NgR polypeptide of claim 1, wherein said polypeptide comprises at least 15 consecutive amino acids of said full length human NgR R377Q or R377W mutant.

6. The isolated NgR polypeptide of claim 1, wherein said polypeptide comprises at least 20 consecutive amino acids of said full length human NgR R377Q or R377W mutant.

7. The isolated NgR polypeptide of claim 1, wherein said polypeptide comprises at least 25 consecutive amino acids of said full length human NgR R377Q or R377W mutant.

8. The isolated NgR polypeptide of claim 1, wherein said polypeptide comprises at least 30 consecutive amino acids of said full length human NgR R377Q or R377W mutant.

9. The isolated NgR polypeptide of claim 8, wherein said polypeptide comprises an amino acid sequence selected from the group consisting of:

```
(a)  VPPGDSPPGNGSGPQHINDSPFGTLPGSAE;  (SEQ ID NO: 1)

(b)  RVPPGDSPPGNGSGPQHINDSPFGTLPGSA;  (SEQ ID NO: 2)

(c)  VPPGDSPPGNGSGPWHINDSPFGTLPGSAE;  (SEQ ID NO: 3)

and (d)  RVPPGDSPPGNGSGPWHINDSPFGTLPGSA.  (SEQ ID NO: 4)
```

10. The isolated NgR polypeptide of claim 1, wherein said polypeptide comprises amino acids 311 to 473 of said full length human NgR R377Q or R377W mutant.

11. An isolated polypeptide comprising the NgR polypeptide of claim 1 attached to at least one heterologous moiety selected from the group consisting of:
   (a) a serum albumin;
   (b) an Fc region;
   (c) a signal peptide; and
   (d) a polypeptide tag.

12. The isolated polypeptide of claim 11, wherein said heterologous moiety is attached to the N-terminal amino acid of said NgR polypeptide.

13. The isolated polypeptide of claim 11, wherein said heterologous moiety is attached to the C-terminal amino acid of said NgR polypeptide.

14. An isolated polypeptide comprising the NgR polypeptide of claim 1 attached to one or more polyalkylene glycol moieties.

15. An isolated polypeptide comprising the NgR polypeptide of claim 1, wherein said polypeptide is soluble.

16. A pharmaceutical composition comprising the isolated NgR polypeptide of claim 1 and a pharmaceutically acceptable carrier or diluent.

17. An isolated polynucleotide comprising a nucleotide sequence that encodes the NgR polypeptide of claim 1.

18. A vector comprising the polynucleotide of claim 17.

19. A host cell comprising the vector of claim 18.

20. An isolated polynucleotide comprising a nucleotide sequence that encodes an amino acid sequence selected from the group consisting of:

```
(a)  VPPGDSPPGNGSGPQHINDSPFGTLPGSAE;  (SEQ ID NO: 1)

(b)  RVPPGDSPPGNGSGPQHINDSPFGTLPGSA;  (SEQ ID NO: 2)

(c)  VPPGDSPPGNGSGPWHINDSPFGTLPGSAE;  (SEQ ID NO: 3)

and (d)  RVPPGDSPPGNGSGPWHINDSPFGTLPGSA.  (SEQ ID NO: 4)
```

21. A method of suppressing neuronal cell growth inhibition in vitro, said method comprising contacting a neuronal cell that expresses a Nogo receptor with:
   (a) an agent that causes NgR-mediated growth inhibition; and
   (b) the isolated NgR polypeptide of claim 1.

* * * * *